United States Patent
Kuth et al.

(10) Patent No.: US 7,707,043 B2
(45) Date of Patent: Apr. 27, 2010

(54) METHOD TO INPUT AND STORE DATA FOR A CLINICAL STUDY

(75) Inventors: Rainer Kuth, Herzongenaurach (DE); Karsten Wicklow, Limhamn (SE)

(73) Assignee: Siemens AG, Munich (DE)

( * ) Notice: Subject to any disclaimer, the term of this patent is extended or adjusted under 35 U.S.C. 154(b) by 1115 days.

(21) Appl. No.: 10/780,211

(22) Filed: Feb. 17, 2004

(65) Prior Publication Data
US 2004/0176986 A1    Sep. 9, 2004

(30) Foreign Application Priority Data
Feb. 14, 2003    (DE) ................ 103 06 271

(51) Int. Cl.
G06Q 10/00    (2006.01)
G06Q 50/00    (2006.01)
A61B 5/00    (2006.01)
G06F 19/00    (2006.01)

(52) U.S. Cl. ............................. 705/2; 705/3

(58) Field of Classification Search ............... 705/2–4
See application file for complete search history.

(56) References Cited

U.S. PATENT DOCUMENTS

| | | | |
|---|---|---|---|
| 5,734,883 A * | 3/1998 | Umen et al. ................ 707/1 |
| 6,272,470 B1 * | 8/2001 | Teshima ..................... 705/3 |
| 6,496,827 B2 | 12/2002 | Kozam et al. | |
| 6,729,882 B2 * | 5/2004 | Noble ......................... 434/167 |
| 2002/0035487 A1 * | 3/2002 | Brummel et al. ............. 705/3 |
| 2003/0013951 A1 * | 1/2003 | Stefanescu et al. ......... 600/407 |
| 2003/0033168 A1 * | 2/2003 | Califano et al. ............. 705/3 |
| 2003/0206646 A1 * | 11/2003 | Brackett ..................... 382/128 |
| 2003/0208378 A1 * | 11/2003 | Thangaraj et al. ........... 705/2 |
| 2004/0059597 A1 * | 3/2004 | Tkaczyk et al. ............. 705/2 |
| 2004/0176986 A1 * | 9/2004 | Kuth et al. ................... 705/3 |
| 2005/0110788 A1 * | 5/2005 | Turner et al. ............... 345/419 |

FOREIGN PATENT DOCUMENTS

DE    100 22 039 A1    4/2001

OTHER PUBLICATIONS

Unique. (2007) In Good Word Guide, Retrieved Jul. 10, 2008.*
Oracle Clinical data sheet, Aug. 2002.*
Oracle Clinical, Remote Data Capture 2001.*
Oracle Cinical User Group Meeting, 2002.*
Prosys 1997 Business process Framework.*
Siebel eClinical7.*

* cited by examiner

*Primary Examiner*—C. Luke Gilligan
*Assistant Examiner*—Neal R Sereboff
(74) *Attorney, Agent, or Firm*—Schiff Hardin LLP

(57) ABSTRACT

A method provides for inputting and storing data for a clinical study in a uniform manner by different study locations. Accordingly, the method comprises generation of an input platform program for an input of data of a clinical study, distribution of the input platform to input locations, calling up and activating the input platform program dependent on a participant characteristic linked with a study participant in the clinical study, inputting the data at an input location via an input platform generated by the input platform program, and storing the input data.

7 Claims, 2 Drawing Sheets

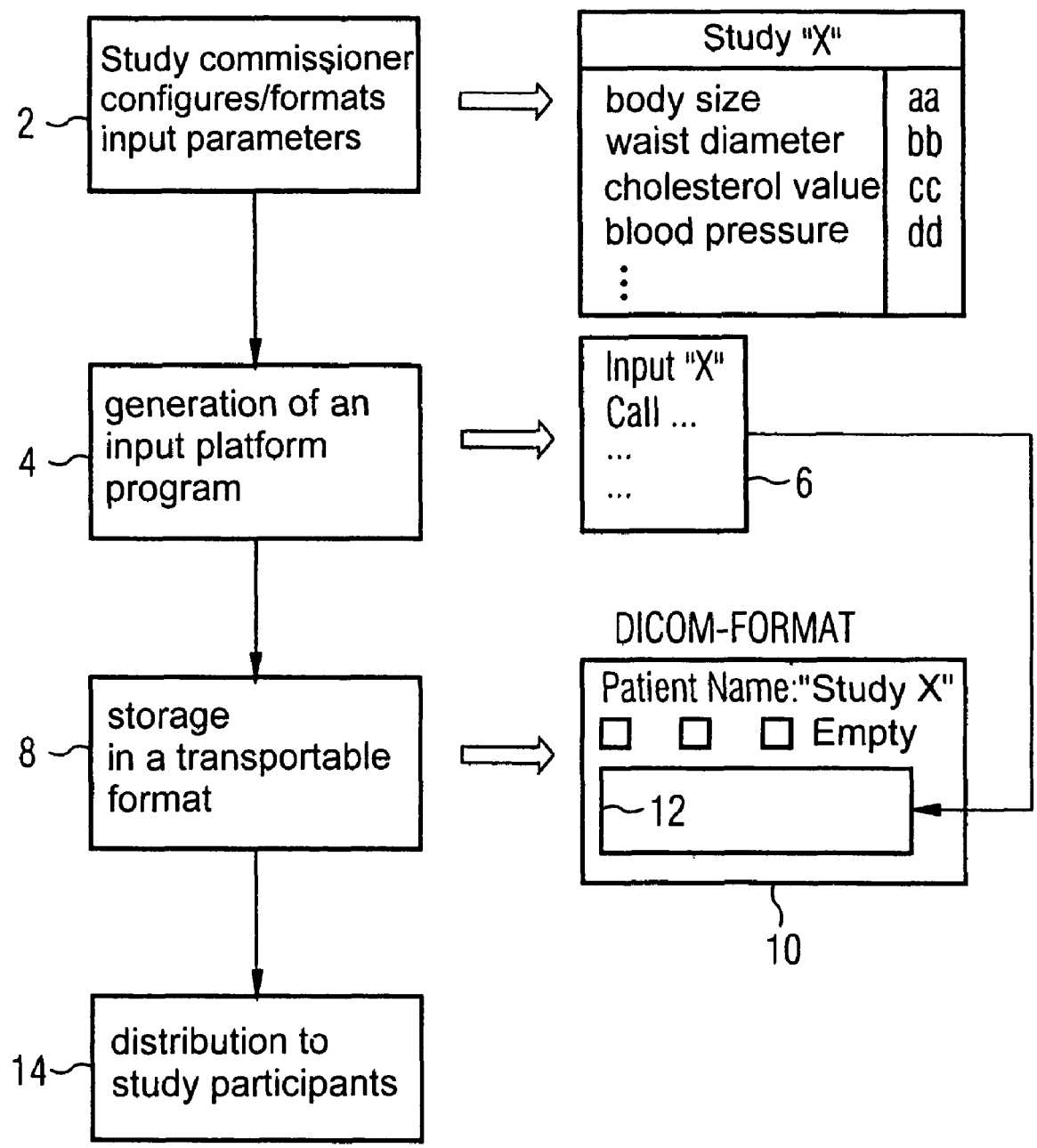

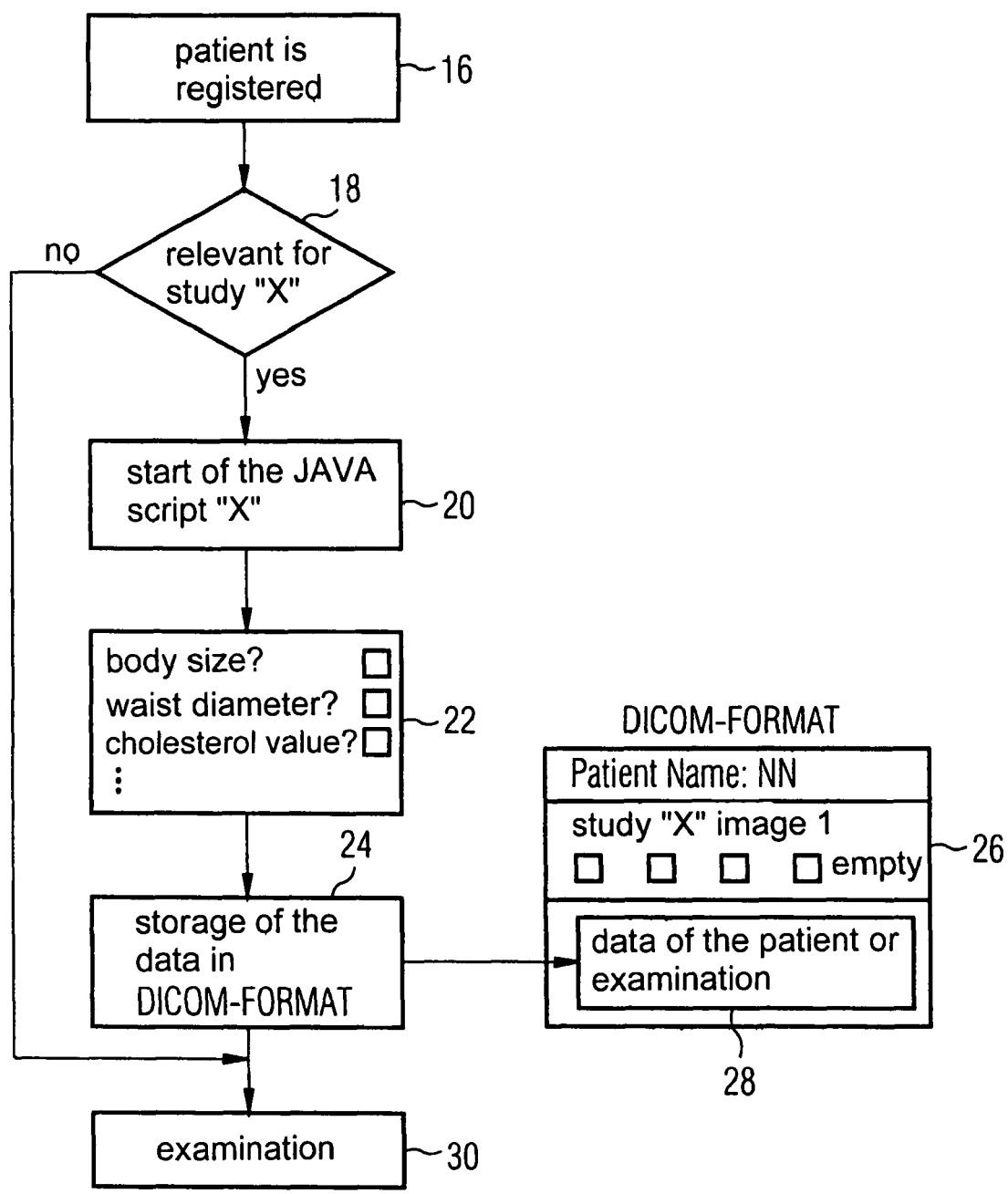

METHOD TO INPUT AND STORE DATA FOR A CLINICAL STUDY

BACKGROUND OF THE INVENTION

The efficacy and harmlessness of newly developed pharmaceuticals is often proven in the framework of a clinical study with as many study participants as possible. Pharmaceuticals are defined as chemical compounds or preparations that develop a therapeutic effect in people and/or animals, or as auxiliary chemicals (e.g., contrast agents) that support or, in many cases, first enable the diagnosis of a disease.

To implement such a study, for example, pharmaceutical producers normally conclude cooperation agreements with a plurality of clinics that have the clinics, among other things, undertake in particular documentation with special diligence. In the clinical study, incidental data are generated and also documented within a single clinic at a plurality of locations, for example, at diagnostic or other medical devices. A summarizing documentation requires a high organizational effort. This problem is multiplied when, as is typical, a plurality of clinics participate in a study. Additionally, study data are for the most part stored in different logical formats. Thus some clinics write study data with word processing programs, others use data processing programs for it, etc.

An Internet-based method to implement a clinical study is specified in German patent document DE 100 22 039, in which study forms are made available worldwide from a central server (study server) to arbitrary locations after an authorization check. This enables the authors of the study to store the determined results directly on the study server. To implement the study, the participating doctor can call up the study protocol on the websites of the study server after authorization. The doctor follows the instructions that he receives via the websites and enters all of the data material that he has obtained in the execution of the study into the data templates provided.

Standards for a patient information system have been developed for medical devices that allow data to be transmitted and stored without information loss in a heterogeneous infrastructure (as is present in a clinic, a medical practice, or a medical laboratory), even when the devices communicating with one another cannot fully understand transmitted information. It suffices that specific information exists in a standardized format for transmission and storage, for example, address information, information about the data type, etc.

An example of such a standard is the DICOM standard (DICOM=Digital Imaging and Communication). DICOM standardizes the structure of the formats and descriptive parameters for radiological images and commands to exchange these images, but also the specification of other data objects such as frame rate, examination series and findings. The specification of different methods for data compression is also established in DICOM. The DICOM standard is differentiated, roughly speaking, into three different areas or blocks. A first set defined general block that is binding for all producers and modalities comprises instructions to order and distribute data. Furthermore, a modality-specific block is defined that is binding for all producers. Found in this block, for example in the case of magnetic resonance imaging, are the parameters (echo time, repetition time, etc.) thereby used. Finally, there are proprietary blocks that each producer can complete for his own purposes.

SUMMARY OF THE INVENTION

The invention is now based on the object to provide a method to input and store data for a clinical study that enables a simple, complete, and secure input of study data, while at the same time permitting a simple evaluation of the study.

The preceding object is achieved by the following method steps:
  generating an input platform program for an input of data of a clinical study,
  distributing the input platform program to input locations,
  calling up and activating the input platform program dependent on a participant characteristic, whereby the participant characteristic is linked with a patient participating in the clinical study,
  inputting the data at an input location via the input platform, and
  storing the input data.

This method ensures that, in a clinical study, identical input platforms are generated at all participating input locations, via which only such data can be input that are required for precisely this clinical study and that are incurred at the current input location in the examination of the study participant. The type of the data input and data storage is always the same, not only within an individual clinic, but rather also for a plurality of participating clinics. Even when the input locations are spatially separated by a great distance and are organized very differently, a uniform and complete recording, and thus also a simple evaluation of the study data, is therewith possible.

A particularly advantageous embodiment provided having the input platform program being distributed in the framework of a medical data standard. The storage and distribution in a medical data format is therefore particularly suited for use in a clinical study because this format can be handled well by diagnosis devices used in the clinic, in particular imaging systems and also other therapy devices. A further advantage is the wide compatibility, both with the existing infrastructure of medical devices and a compatibility with different software versions as they are to be expected inside the typical time span of a study.

A further particularly advantageous embodiment is characterized in that the storage of the data recorded at the input location ensues in a data format that is set by the input platform itself. It is therewith ensured that the data format of the data generated at the various input locations is the same. The evaluation of the data itself is therewith possible without further processing of the data, and thus also significantly simplified.

The retrieval of the recorded data is simplified in a further advantageous embodiment, in that these recorded data are in turn stored in a region of the medical data standard reserved for patient data.

DESCRIPTION OF THE DRAWINGS

An exemplary embodiment of the invention is explained in the following suing two figures.

FIG. 1 is a flow diagram illustrating the substantial method steps to generate an input platform; and FIG. 2 is a flow diagram illustrating the substantial method steps to record and to store data determined in a clinical study.

DETAILED DESCRIPTION OF THE PREFERRED EMBODIMENTS

According to an exemplary embodiment of the invention, if, for example, a clinical study of the therapeutic effect of a new medicine is commissioned by a pharmaceutical producer, the pharmaceutical producer as the study commissioner first configures and/or formats input parameters (step 2) that are required for this study. As an example, in FIG. 1 the input parameters for a study X are determined as body size with a field "aa", waist diameter with a field "bb", cholesterol value with a field "cc", and blood pressure with a field "dd". Using these specifications, in a next step 4, an input platform program 6 is now generated. The input platform program 6 comprises instructions for generation of input templates and input methods and is programmed in a suitable high-level language, for example JAVA. The input platform program 6 is now stored (step 8) in a transportable format corresponding to a medical data standard. In this case, the prevalent DICOM standard is used (step 10). Data to identify the study (here in the field "patient name") are thereby stored in the header, and the individual instructions of the input platform program 6 are stored in a field or block 12 which is provided in the DICOM standard to store patient-specific image data. The input platform program 6 is distributed (step 14) in this format to input locations that participate in the corresponding study.

The input platform program 6 can be simply be distributed in the framework of the DICOM standard via the use of the JAVA programmer model, which in particular enables a storage as packets (serializing). Requirements for the data security, authenticity and integrity are thereby ensured.

The substantial steps to input and store the study data are summarized in FIG. 2. After a patient has been registered at a specific examination station that is provided for the clinical study as an input location, the patient data are queried in the following step 18 as to whether and in which form this patient participates in a specific study. Given a positive query result, the input platform program 6 distributed for the provided study is started in the next step 20 according to the yes-path. The input platform program 6 thereupon generates input fields 22 that define the data to be surveyed, provide corresponding input fields, and prescribe data formats for storage. After input of the queried data, these are subject to a plausibility test in which it is asked whether the input data are in the range specified by the study commissioner. The input data are stored (in the following step 24 in a medical data format 26) in a corresponding medical archiving system as it is set by the input platform program 6. A field or block 28 is also provided for this in which examination data of the patient are stored by default. From there, the appertaining data can be queried and evaluated with regard to the study.

After conclusion of the data input for the study, medical examinations 30 of the patient follow that are provided at the examination station independent of the study. By way of avoiding the start of the input platform program 6, the same examinations 30 are implemented immediately, corresponding to the no-path, when the corresponding patient is not participating in the study.

With the preceding method, it is possible at any time, particularly also after delivery of operating software for clinical devices to the client, to subsequently establish and to implement in the individual clinics (and there at the input locations) uniform input platforms and data formats for clinical studies. The study commissioner can thereby set which data are required and in which format they should be stored. For this, the operating software must only be expanded in the field "patient information system", such that the fields provided for patient data can additionally comprise objects that comprise program code and/or data.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

REFERENCE LIST 2 configure
4 generate program
6 input platform program
8 store
10 format
12 block
14 distribute
16 register patient
18 relevance test
20 start program
22 input field
24 store
26 data format
28 block
30 exam

What is claimed is:

1. A method to input and electronically store data for a medical clinical study, comprising the steps of:

through user interaction with a processor, generating a customized input platform program comprising programming instructions that operate a computer workstation having a display, that cause a collection of computer input fields to be presented at said display with said computer input fields configured only and precisely for entry, into a computer at which said input fields are displayed, of the data that is necessary for a specific medical clinical study;

from said processor, electronically distributing said customized input platform program, to respective storage locations established by said customized input platform according to the DICOM standard, at each of a plurality of computer workstations each having a display, respectively located at input locations with which patients participating in the specific medical clinical study interface;

upon interfacing at one of said input locations with one of said patients, entering a characteristic identifying that patient into the computer workstation at said one of said input locations and, via the computer workstation, automatically calling and activating said customized input platform program solely for said specific medical clinical study solely by entry of said characteristic into said computer workstation;

via said display of said computer workstation at said one of said input locations, providing data for said specific medical clinical study only by making entries, through said computer workstation, in respective input fields of the collection of input fields caused by said customized input platform program to be presented at the computer at the display of the computer workstation at the input location; and electronically storing the data entered via the customized input platform program to generate an electronically accessible database for said customized input platform program and making said database electronically accessible to participants in said specific medical clinical study.

2. The method according to claim 1, further comprising electronically storing the customized input platform program in a region of the electronically storable medical data standard reserved for patient data.

3. The method according to claim 1 comprising electronically storing the acquired data in a framework of an electronically storable medical data standard.

4. The method according to claim 3 comprising electronically storing the acquired data in a region of the electronically storable medical data standard reserved for patient data.

5. The method according to claim 1 comprising distributing the customized input platform program a framework of the Digital imaging and Communication in Medicine (DICOM) standard, as said electronically storable medical standard.

6. The method according to claim 1 comprising, via said input platform, permitting only inputs into said collection of input fields that are required for said specific medical clinical study and that are incurred at the input locations that interface with patients participating in the specific medical clinical study.

7. The method according to claim 1 comprising generating the customized input platform program by a research entity commissioning the specific medical clinical study.

* * * * *